United States Patent [19]
Bucci

[11] Patent Number: 6,117,429
[45] Date of Patent: Sep. 12, 2000

[54] COMPOSITIONS AND TREATMENTS FOR REDUCING POTENTIAL UNWANTED SIDE EFFECTS ASSOCIATED WITH LONG-TERM ADMINISTRATION OF ANDROGENIC TESTOSTERONE PRECURSORS

[75] Inventor: Luke R. Bucci, West Valley City, Utah

[73] Assignee: Weider Nutrition International, Inc, Salt Lake City, Utah

[21] Appl. No.: 09/132,359

[22] Filed: Aug. 11, 1998

Related U.S. Application Data

[60] Provisional application No. 60/055,346, Aug. 11, 1997.

[51] Int. Cl.$^7$ ................................................. A61K 35/78
[52] U.S. Cl. ..................... 424/195.1; 424/641; 514/169; 514/170
[58] Field of Search ........................ 424/195.1, 641; 514/169, 170

[56] References Cited

U.S. PATENT DOCUMENTS

| | | | |
|---|---|---|---|
| 3,647,829 | 3/1972 | Kruger | 552/609 |
| 4,014,988 | 3/1977 | Pharriss et al. | 424/432 |
| 4,016,270 | 4/1977 | Pharriss et al. | 514/174 |
| 4,054,651 | 10/1977 | Benson et al. | 514/177 |
| 4,100,026 | 7/1978 | Weber et al. | 435/55 |
| 4,100,027 | 7/1978 | Weber et al. | 435/55 |
| 4,170,518 | 10/1979 | Weber et al. | 435/55 |
| 4,235,893 | 11/1980 | Brodie et al. | 514/178 |
| 4,331,657 | 5/1982 | Cox et al. | 424/158.1 |
| 4,457,914 | 7/1984 | Cox et al. | 424/194.1 |
| 4,474,701 | 10/1984 | Teichmuller et al. | 552/638 |
| 4,500,523 | 2/1985 | Nathanielsz | 514/178 |
| 4,749,567 | 6/1988 | McNatty et al. | 424/194.1 |
| 4,920,115 | 4/1990 | Nestler et al. | 514/178 |
| 4,946,701 | 8/1990 | Tsai et al. | 426/597 |
| 5,028,600 | 7/1991 | Jeppsson | 514/182 |
| 5,116,828 | 5/1992 | Miura et al. | 514/171 |
| 5,166,200 | 11/1992 | Fujise et al. | 514/177 |
| 5,183,815 | 2/1993 | Saari et al. | 514/172 |
| 5,206,008 | 4/1993 | Loria | 424/45 |
| 5,227,375 | 7/1993 | Labrie et al. | 514/172 |
| 5,277,907 | 1/1994 | Loria | 424/93.71 |
| 5,296,481 | 3/1994 | Partridge et al. | 514/178 |
| 5,372,822 | 12/1994 | Fahim | 424/643 |
| 5,387,583 | 2/1995 | Loria | 514/171 |
| 5,391,776 | 2/1995 | Ueno et al. | 552/507 |
| 5,418,145 | 5/1995 | Webber et al. | 435/55 |
| 5,420,120 | 5/1995 | Boltralink | 514/172 |
| 5,424,463 | 6/1995 | Lardy et al. | 552/637 |
| 5,446,070 | 8/1995 | Mantelle | 514/772.6 |
| 5,461,042 | 10/1995 | Loria | 514/182 |
| 5,489,581 | 2/1996 | Daynes et al. | 514/170 |
| 5,506,223 | 4/1996 | Lardy et al. | 514/178 |
| 5,516,649 | 5/1996 | Weber et al. | 435/55 |
| 5,527,552 | 6/1996 | Todd, Jr. | 426/541 |
| 5,532,230 | 7/1996 | Daynes et al. | 514/178 |
| 5,536,714 | 7/1996 | Kojima et al. | 514/169 |
| 5,545,634 | 8/1996 | Labrie | 514/169 |
| 5,565,444 | 10/1996 | Mizushima et al. | 514/178 |
| 5,578,588 | 11/1996 | Mattern et al. | 514/177 |
| 5,583,126 | 12/1996 | Daynes et al. | 514/170 |
| 5,583,128 | 12/1996 | Bhatnagar | 514/177 |
| 5,585,371 | 12/1996 | Lardy | 514/171 |
| 5,587,369 | 12/1996 | Daynes et al. | 514/178 |
| 5,635,496 | 6/1997 | Daynes et al. | 514/169 |
| 5,641,768 | 6/1997 | Loria | 514/182 |
| 5,719,197 | 2/1998 | Kanios et al. | 514/772.6 |
| 5,728,688 | 3/1998 | Labrie | 514/178 |
| 5,776,923 | 7/1998 | Labrie | 514/176 |
| 5,780,086 | 7/1998 | Kirksey et al. | 426/330.3 |
| 5,780,460 | 7/1998 | Labrie | 514/178 |
| 5,798,347 | 8/1998 | Labrie | 514/178 |
| 5,804,576 | 9/1998 | Schwartz et al. | 514/177 |
| 5,807,849 | 9/1998 | Labrie | 514/178 |
| 5,824,671 | 10/1998 | Labrie | 514/178 |
| 5,837,700 | 11/1998 | Labrie | 514/178 |
| 5,843,932 | 12/1998 | Labrie | 514/178 |
| 5,854,229 | 12/1998 | Labrie | 514/169 |
| 5,872,114 | 2/1999 | Labrie | 514/178 |

FOREIGN PATENT DOCUMENTS

| | | |
|---|---|---|
| 0 424 954 A1 | 10/1990 | European Pat. Off. . |
| WO 93/21924 | 11/1993 | WIPO . |

OTHER PUBLICATIONS

Larue, J.P., Morfin, R.F., Charles, J.F. Le zinc dans la prostate humaine. Journal d'Urologie, 91, No. 7, (1985) pp. 463–468. [English Abstract].

Habenicht, Ursula–F, Schwarz, Klaus, Schweikert, Hans–U., Neumann, Friedmund, El Etreby, M. Fathy. Development of a Model for the Induction of Estrogen–Related Prostatic Hyperplasia in the Dog and its Response to the Aromatase Inhibitor 4–Hydroxy–4–Androstene–3, 17–Dione: Preliminary Results. The Prostate 8: (1986) pp. 181–194.

(List continued on next page.)

*Primary Examiner*—Jean C. Witz
*Attorney, Agent, or Firm*—Parsons Behle & Latimer

[57] ABSTRACT

A method for reducing potential adverse effects of androgenic testosterone precursors by interfering with production or action of testosterone and estrogen metabolites by nutrient combinations is described. Although androgenic testosterone precursors themselves have little or no toxicity, there is the potential for their metabolites, estradiol and dihydrotestosterone, to enhance or cause hormone-responsive illnesses such as breast or prostatic cancer, benign prostatic hyperplasia, or hirsutism or acne in women. The use of the invented nutrient combinations reduces the formation or action of estradiol and dihydrotestosterone, thereby reducing potential adverse effects from increased production of these hormones following androgenic testosterone precursor administration. This may be accomplished without negating the effects of testosterone on muscle anabolism. The nutrient combinations include androstenedione, DHEA, pregnenolone, androstenediols, norandrostenedione and norandrostenediols, and natural products which reduce estrogen effects in the estrogen-responsive tissues, and substances to reduce formation of dihydrotestosterone from testosterone in prostate tissue.

20 Claims, 1 Drawing Sheet

OTHER PUBLICATIONS

Habenicht, Ursula–F., El Etreby, M. Fathy. Synergic Inhibitory Effects of the Aromatase Inhibitor 1–Methyl–Androsta–1, 4–Diene–3, 17–Dione and the Antiandrogen Cyproterone Acetate on Androstenedione–Induced Hyperplastic Effects in the Prostates of Castrated Dogs. The Prostate 11: (1987) pp. 133–143.

Schaeffer, Hans–Jorg, Sirotkin, Alexander V. The Release of Insulin–like Growth Factor–I Luteinized Human Granulosa Cells in Vitro: Regulation by Growth Hormone, Oxytocin, Steroids and cAMP–dependent Intracellular Mechanisms. Experimental and Clinical Endocrinology & Diabetes. 103 (1995) pp. 361–366.

Mastrogiacomo, I, Bonanni, G., Menegazzo, E., Santarossa, C., Pagani, E., Gennarelli, M., Angelini, C. Clinical and Hormonal Aspects of Male Hypogonadism in Myotonic Dystrophy. Italian Journal of Neurological Science, 17: (1996) pp. 59–65.

Bassir, O., Odebiyi, O. Male Virilising Substances in Some Nigerian Medicinal Preparations—Androgenic Steriods. W.A. Journal of Biological and Applied Chemistry. vol. 19, No. 2, (1976). pp. 25–29. DHEA by USA Nutritionals, Drug Store News, p. 39, Jan. 1997.

Yen, S.S.C. et al., Annals of the New York Academy of Sciences, vol. 774, p. 128–142, Dec. 1995.

Arif Adimoella, F.X. et al., International J. of Andrology, vol. 20(1), p. 39, abstract #153, 1997.

Nippon Zoki Pharmaceutical, Oct. 26, 1990.

Winkler, et al., Nov. 11, 1993.

Alen, M., Pakarinen, A., Hakkinen, K. and Komi, P.V. Responses of Serum Androgenic–Anabolic and Catabolic Hormones to Prolonged Strength Training. Int. J. Sports Med. vol. 9 (1988). pp. 229–233.

Abrahamsson, G., Janson, P.O., and Kullander, S. Steroid Release From Two Human Epithelial Ovarian Tumors: Evidence For An Intrinsic Production in Vitro. Gynecologic Oncology, vol. 64 (1997), pp. 64, 99–104.

Auzeby, A., Bogdan, A., and Touitou, Y.. An Alternate Pathway to Androstenedione Syntheses by Human Adrenals: Evidence of a Balance in 11$\beta$–Hydroxylase and 17,20–Lyase Activities Leading to Androstenedione. Journal of Clinical Endroclinology and Metabolism, vol. 80, No. 5 (1995), pp. 1706–1711.

Barrett–Connor, Elizabeth, Garland,Cedric, McPhillips, Janice B., Khaw, Kay–Tee, and Wingard, Deborah L. Cancer Research vol. 50 (1990), pp. 169–173.

Bartsch, Wilfred, Klein, Hartmut, Sturenburg, Hans–Jorg, and Vorgt, Klass–Dieter. Metabolism of Androgens in Human Benign Prostatic Hyperplasia: Aromatase and its Inhibition. Steriod Biochem, vol. 27, No. 1–3 (1987), pp. 557–564.

Begin, D., Luthy, I.A., and Labrie, F. Adrenal Precursor $C^{19}$ Steriods are Potent Stimulators of Growth of Androgen–Sensitive Mouse Mammary Carcinoma Shionogi Cells in Vitro. Molecular and Cellular Endocrinology, vol. 58 (1988), pp. 213–219.

Belisle, Serge, Lehoux, Jean–Guy, and Brault, Jacques. The Metabolism of Androstenedione in Human Pregnancy: The Use of Constant Infusion of Unlabeled Steriod to Assess Its Metabolic Clearance Rate, Its Production Rate, and Its Conversion into Androgens and Estrogens. American Journal of Obstetrics and Gynecology, vol. 136, No. 8 (1980), pp. 1030–1035.

Belisle, Serge, Osathanondh, Rapin, and Tulchinsky, Dan. The Effect of Constant Infusion of Unlabeled Dehydroepiandrosterone Sulfate on Maternal Plasma Androgens and Estrogens. Journal of Clinical Endocrinology and Metobolism, vol. 45, No. 3 (1977), pp. 544–550.

Brodie, A.M.H., Son, C., King, D.A., Meyer, K.M. and Inkster, S.E. Lack of Evidence for Aromatase in Humkan Prostatic Tissues: Effects of 4–Hydroxyandrostenedione and Other Inhibitors on Androgen Metabolism. Cancer Research vol. 49 (1989), pp. 6550–6555.

Bulun, Serdar E., Simpson, Evan R., and Word R. Ann. Expression of the CYP 19 Gene and Its Propduct Aromatase Cytochrome P450 in Human Uterine Leiomyoma Tissues and Cells in Culture. Journal of Clinical Endocrinology and Mebabolism, vol. 78, No. 3 (1994), pp. 736–743.

Cauley, Jane A., Gutai, James P., Kuller, Lewis H., LeDonne, Dorothea, and Powell, John G. The Epidemiology of Serum Sex Hormones in Postmenopausal Women. American Journal of Epidemiology, vol. 129, No. 6 (1989), pp. 1120–1131.

Collins, Bridgette M., McLachlan, John A. and Arnold, Steven F. The Estrogenic and Antiestrogenic Activities of Phytochemicals with the Human Estrogen Receptor Expressed in Yeast. Steroids, vol. 62 (1997), pp. 365–372.

Crave, Jean–Charles, Fimbel, Sylvie, Lejeune, Herve, Cugnardney, Nathalie, Dechaud, Henri, and Pugeat, Michael. Effects of Diet and Metformin Administration on Sex Hormone–Binding Globulin, Androgens, and Insulin in Hirsute and Obese Women. Journal of Clinical Endocrinology and Metabolism, vol. 80, No. 7 (1995), pp. 2057–2062.

Deslypere, J.P., and Vermeulen, A. Aging and Tissue Androgens. Journal of Clinical Endocrinology and Metabolism, vol. 53, No. 7 (1981), pp. 430–434.

Deslypere, J.P., and Vermeulen, A. Influence of Age on Steroid Concentrations in Skin and Striated Muscle in Women and in Cardiac Muscle and Lung Tissue in Men. Journal of Clinical Endocrinology and Metabolism, vol. 61 (1985), pp. 648–653.

Deslypere, J.P., Sayed, A., Verdonck, L, and Vermeulen, A. Androgen Concentrations in Sexual and Non–Sexual Skin as Well as in Striated Muscle in Man. Journal of Steroid Biochemistry, vol. 13 (1980), pp. 1455–1458.

Garrouj, Driss El, Aumelas, Andre and Borgna, Jean–Lois. Steroidal Affinity Labels of the Estrogen Receptor. 1. 17$\alpha$–(Bromoacetoxy)alkyl/alkynylestradiols. Journal of Medicinal Chemistry, vol. 36 (1993), pp. 2973–2983.

Fahim, M.S., Fahim, Z., Der, R., and Harman, J. Zinc Treatment For Reduction of Hyperplasia of Prostate. Federation Proc. vol. 35 (1976), pp. 361. (Abstract).

Feustel, A., and Wennrich, R. Zinc and Cadmium in Cell Fractions of Prostatic Cancer Tissues of Different Histological Grading in Comparsion to BPH and Normal Prostate. Urological Research, vol. 12 (1984), pp. 147–150.

Gann, Peter H., Hennekens, Charles H., Longcope, Christopher, Verhoek–Oftedahl, Wendy, Grodstein, Francine, and Stampfer, Meir J. A Prospective Study of Plasma Hormone Levels, Nonhormonal Factors, and Development of Benign Prostatic Hyperplasia. The Prostrate, vol. 26 (1995), pp. 40–49.

Guthrie, Najila, Gapor, Adbul, Chambers, Ann F., and Carroll, Kenneth K. Inhibition of Proliferation of Estrogen Receptor–Negative MDA–MB–435 and —Positive MCF–7 Human Breast Cancer Cells by Palm Oil Tocotrienols and Tamoxifen, Alone and in Combination. Journal of Nutrition, vol. 127 (1997), pp. 544S–548S.

Habenicht, Ursula F. and El Etreby, M. Fathy. Selective Inhibition of Androstenedione–Induced Prostate Growth in Intact Beagle Dogs by a Combined Treatment with the Antiandrogen Cyproterone Acetate and the Aromatase Inhibitor 1–Methyl–Androsta–1, 4–Diene–3, 17–Dione (1–Methyl–ADD), The Prostate. vol. 14 (1989), pp. 309–322.

Habenicht, Ursula F, El Etreby,M. Fathy, Lewis, Ronald, Ghoniem, Gamal, and Roberts, James. Induction of Metachromasia in Experimentally Induced Hyperplastic/Hypertrophic Changes in the Prostrate of the Cynomolgus Monkey (Macaca Fascicularis). The Journal of Urology, vol. 142 (1989), pp. 1624–1626.

Habib, F.K., Hammond, G.L., Lee, I.R., Dawson, J.B., Mason, M.K., Smith P.H., and Stitch, S.R. Metal–Androgen Interrelationships in Carcinoma and Hyperplasia of the Human Prostate. Journal of Endocrinology, vol. 71 (1976), pp. 133–141.

Hammond, G.L., Kontturi, M., Vihko, P., and Vihko, R. Serum Steroids in Normal Males and Patients with Prostatic Diseases. Clinical Endocrinology, vol. 9 (1978), pp. 113–121.

Harper,M.E., Peeling,W.T., Cowley,T., Brownsey,B.G., Phillips, M.E.A.,Groom, G., Fahmy, D.R., and Griffiths, K. Plasma Steroid and Protein Hormone Concentrations in Patients With Prostatic Carcinoma. Before and During Oestrogen Therapy. Acta Endocrinologica, vol. 81 (1976), pp. 409–426.

Hill, P., Wynder, E.L., Garbaczewski, L., Garnes, H. and Walkerm A.R.P. Response to Luteinizing Releasing Hormone, Thyrotrophic Releasing Hormone, and Human Chorionic Gonadotrophin Administration in Healthy Men at Different Risks for Prostatic Cancer and in Prostatic Cancer Patients. Cancer Research, vol. 42 (1982), pp. 2074–2080.

Kaburagi, Yutaka, Marino, Michael B., Kirdani, Rashad Y., Greco, Jospeh P., Karr, James P., and Sandberg, Avery A. The Possibility of Aromatization of Androgen in Human Prostate. J.Steroid Biochem, vol. 26, No. 6. 91987), pp. 739–742.

Kellis, James T. Jr., and Vickery, Larry E. Inhibition of Human Estrogen Synthetase (Aromatase) by Flavones. Science vol. 225 (1984), pp. 1032–1034.

Kiddy, D.S., Hamilton–Fairley, D., Seppala, M., Koistinen, R., James, V.H.T., Reed, M.J., and Franks, S. Diet–Induced Changes in Sex Hormone Binding Globulin and Free Testosterone in Women with Normal or Polycystic Ovaries: Correlation With Serum Insulin and Insulin–Like Growth Factor–I. Clinical Endocrinilogy, vol. 31 (1989), pp. 757–763.

Leake, Alan, Chisholm, Geoffrey D., and Habib, Fouad K. The Effect of Zinc on the 5α–Reduction of Testosterone by the Hyperplastic Human Prostate Gland. J.Steroid Biochem, vol. 20, No. 2. (1984), pp. 651–655.

Leenen, R., van der Kooy, K., Seidell, J.C., Deurenberg, P. and Koppeschaar, H.P.F. Visceral Fat Accumulation in Relation to Sex Hormones in Obese Men and Women Undergoing Weight Loss Therapy. Journal of Clinical Endocrinology and Metabolism, vol. 78, No. 6, (1994), pp. 1514–1521.

Lobaccaro, Carole, Pons, Jean–Francis, Duchesne, Marie-–Josephe, Auzou, Gilles, Pons, Michel, Nique, Francois, Teutsch, Georges, and Borgna, Jean–Louis. Steroidal Affinity Labels of the Estrogen Receptor. 3. Estradiol 11β–n–Alkyl Derivatives Bearing a Terminal Electrophilic Group: Antiestrogenic and Cytotoxic Properties. J. Med. Chem. vol. 40 (1997), pp. 2217–2227.

Longcope, Christopher, Pratt, J. Howard, Schneider, Stephen H., and Fineberg, S. Edwin. Aromatization of Androgens by Muscle and Adipose Tissue in Vivo, Journal of Clinical Endocrinology and Metabolism, vol. 46, No. 1 (1978), pp. 146–152.

Longcope, C., Billiar, R.B., Takaoka, Y., Reddy, P.S., Richardson, D., and Little, B. Tissue Sites of Aromatization in the Female Rhesus Monkey. Journal of Clinical Endocrinology and Metbolism, vol. 113, No. 5 (1983), pp. 1679–1682.

Mahesh, Virenda B., and Greenblatz, Robert B. The In Vivo Conversion of Dehydroepiandrosterone and Androstenedione to Testosterone in the Human. Acta Endocrinologica, vol. 41 (1962), pp. 400–405.

Martini, L., Celotti, F., Lechuga, M.J., Melcangi, R.C., Motta, M., Negri–Cesi, P., Poletti, A., and Zoppi S. Androgen Metabolism in Different Target Tissues. Annals New York Academy of Sciences, vol. 595 (1990), pp. 184–198.

Matsumine, Hiroto, Hirato, Kumiko, Yanaihara, Takumi, Tamada Taro, and Yoshida, Mitsuo. Aromatization by Skeletal Muscle. Journal of Clinical Endocrinology and Metabolsim, vol. 63, No. 3 (1986), pp. 717–720.

Nestler, John E., Barlascini, Cornelius O., Clore, John N., and Blackard, William G. Dehydroepiandrosterone Reduces Serum Low Density Lipoprotein Levels and Body Fat But Does Not Alter Insulin Sensitivity in Normal Men. Journal of Clinical Endocrinology and Metabolism, vol. 66 (1986), pp. 57–61.

Nicolas, M.H., Crave, J.C., Fimbel, S., Simean, A., and Pugeat, M. Hyperandrogenie de la Femme Hirsute et Obese. La Press Medicale, vol. 22, No. 1 (Jan., 1993), pp. 19–22.

O'Dea, John P.K., Wieland, Ralph G., Hallberg, Marvin C., Lierena, Luis A., Zorn, Elinor M., and Saul M. Genuth, Saul M. Effect of Dietary Weight Loss on Sex Steroid Binding, Sex Steriods, and Gonadotropins in Obese Postmenopausal Women. Lab. Clin. Med. vol. 93, No. 6 (1979), pp. 1004–1008.

Ogunlewe, J.O., and Osegbe, D.N. Zinc and Cadmium Concentrations in Indigenous Blacks with Normal, Hypertrophic, and Malignant Prostate. Cancer, vol. 63, No. 7 (1989). pp. 1388–1392.

Partin, Alan W., Oesterling, Joseph E., Epstine, Jonathan I., Horton, Richard, and Walsh, Patrick C. Influence of Age and Endocrine Factors on the Volume of Benign Prostatic Hyperplasia . Journal of Urology, vol. 145 (1991), pp. 405–409.

Oesterling, Joseph E., Epstein, Jonathan I., and Walsh, Patrick C. The Inability of Adrenal Androgens to Stimulate the Adult Human Prostate: an Autopsy Evaluation of Men With Hypogonadotropic Hypogonadism and Panhypopituitarism. The Journal of Urology, vol. 136 (1986), pp. 1030–1035.

Pasquali,R., Antenucci,D., Melchiondra,N., Fabbri,R., Venturoli,S., Patrono,D.,and Capelli,M. Sex Hormones in Obese Premenopausal Women and Their Relationships to Body Fat Mass and Distribution, B Cell Function and Diet Composition. Endocrinol. Invest.,Vol. 10 (1987), pp. 345–350.

Paula, F.J.A., Gouveia, L.M.F.B., Paccola, G.M.G.F., Piccinato, C.E., Moreira, A.C., and Foss, M.C. Androgen–Related Effects on Peripheral Glucose Metbolism in Women with Congenital Adrenal Hyperplasia. Horm. Metab. Res. vol. 26 (1994), pp. 552–556.

De Pergola, G., Triggiani, V., Giorgino, F., Cospite, M.R., Garruti, G., Cignarelli, M., Guastamacchia, E., and Giorgio, R. The Free Testosterone to Dehydroepiandrosterone Sulphate Molar Ratio as a Marker of Visceral Fat Accumulation in Premenopausal Obese Women. International Journal of Obesity, vol. 18 (1994), pp. 659–664.

Polderman, Kees H., Gooren, Louis J.G., and van der Veen, Eduard A. Effects of Gonadal Androgens and Oestrogens on Adrenal Androgen Levels. Clinical Endocrinology, vol. 43 (1995), pp. 415–421.

Radlmaier, Albert, Eickenberg, Hans U., Fletcher, Matthew S., Fourcade, Richard O., Reis Santos, Jose M., van Aubel, and Bono, Aldo V. Estrogen Reduction by Aromatase Inhibition for Benign Prostatic Hyperplasia: Results of a Double–Blind, Placebo–Controlled, Randomized Clinical Trial Using Two Doses of the Aromatase–Inhibitor Atamestane. The Prostate, vol. 29 (1996), pp. 199–208.

Raeside, J.I., Renaud, R.L., and Friendship, R.M. Aromatization of 19–Norandrogens by Porcine Leydig Cells. J. Steroid Biochem., vol. 32, No. 5 (1989), pp. 729–735.

Resko, John A., Ellinwood, William E., Pasztor, Linda M., and Buhl, Allen E. Sex Steroids in the Umbilical Circulation of Fetal Rheus Monkeys From the Time of Gonadal Differentiation. Journal of Clinical Endocrinology and Metabolism, vol. 50, No. 1 (1980), pp. 900–905.

Resko, John A., Ploem, Jan G., and Stadelman, Henry L. Estrogens in Fetal and Maternal Plasma of the Rheus Monkey. Endocrinology, vol. 97, No. 1 (1975), pp. 425–430.

Saden–Krehula, M., Tajic, M., and Kolbah, D. Testosterone, Epitestosterone and androstenedione in the Pollen of the Scotch Pine P. silvestris L. Experimentia, vol. 27 (1973), pp. 108–109.

Schweikert, Hans–Udo, Wolf, Lutz, and Romalo, Gabriela. Oestrogen Formation From Androstenedione in Human Bone. Clinical Endocrinology, vol. 43 (1995), pp. 37–42.

Stomati, M., Hartmann, B., Spinetti, A., Mailand, D., Rubino, S., Albrecht, A., Huber, J., Petraglia, F., and Genazzani, A.R. Effects of Hormonal Replacement Therapy on Plasma Sex Hormone–Binding Globulin, Androgen and Insulin–Like Growth Factor–1 Levels in Postmenopausal Women. J. Endocrinol. Invest., vol. 19 (1996), pp. 535–541.

Stone, N.N., Laudone, V.P., Fair, W.R., and Fishman, J. Aromatization of Androstenedione to Estrogen by Benign Prostatic Hyperplasia, Prostate Cancer and Expressed Prostatic Secretions. Urological Research, vol. 15 (1987), pp. 165–167.

Suzuki, Kazugiro, Ito, Kazuto, Tamura, Yoshimi, Suzuki, Takanori, Honma, Seijiro, and Yamanaka, Hidetoshi. Effect of Aromatase Inhibitor, TZA–2209, on the Prostate of Androstenedione–Treated Castrated Dogs: Changes in Prostate Volume and Histopathological Findings. The Prostate, vol. 28 (1996), pp. 328–337.

Tunn, Sabine, Hochstrate, Holger, Habenicht, Ursula F., and Krieg, Michael. 5α –Reductase Activity in Ephithelium and Stroma of Prostates From Intact and Castrated Dogs Treated With Androstenedione, the Aromatase Inhibitor 1–Methyl–1, 4–Androstadiene–3, 17–Dione, and Cyproterone Acetate. The Prostate, vol. 12 (1988), pp. 243–253.

Wittliff, James L., and Savlov, Edwin D. Estrogen–Binding Capacity of Cytoplasmic Forms of the Estrogen Receptors in Human Breast Cancer. In Estrogen Receptors in Human Breast Cancer, McGuire, W.L., Carbon, P.P., and Vollmer, E.P. (Eds.) (1975), pp. 73–86.

Longcope, C. and Fineberg, S.E. Production and Metabolism of Dihydrotestosterone in Peripheral Tissues. J. Steriod Biochem. 23(4) (1985) pp. 415–419.

Sigmal–Aldrich Fine Chemicals Catalog. Alphabetical List of Compounds. pp. 135.

Aldrich Chemical Catalog. pp. 110.

Stryer, L. "Synthesis of Progesterone and Corticoids." In Biochemistry (San Francisco, W.H. Freeman and Company 1975), pp. 497–498.

Chaikovskii, V.S., Evtinova, I.V., and Bashiraina, O.B. [Steroid levels and androgen receptors in skeletal muscles during adaptation to physical effort]. *Vopr Med Khim* 31(6) : 80–86 (1985).

Dutkiewicz, S. Zinc and magnesium serum levels in patients with benign prostatic hyperplasia (BPH) before and after prazosin therapy. *Mater Med Pol* 27(1):15–17 (1995).

Habenicht, U.F. and Etreby, M.F. Synergic inhibitory effects of the aromatase 1–methyl–androsta–1,4–diene–3, 17–dione and the antiandrogen cypoterone acetate on androstenedione–induced hyperplastic effects in the prostates of castrated dogs. *Prostate* 11(2):133–43 (1987). Abstract Only.

Habenicht, U.F., Schwarz, K., Schweikert, H.U., Neuman, F., and el–Etreby, M.F. Development of a model for the induction of estrogen–related prostatic hyperplasia in the dog and its response to the aromatase inhibitor 4–hydroxy–4–androstene–3–17–dione: preliminary results. *Prostate* 8(2):181–94 (1986). Abstract Only.

Komori, A., Yatsunami, J., Okabe, S., Abe, S., Hara, K., Suganuma, M., Kim, S.J. and Fujiki, H. Anticarcinogenic activity of green tea polyphenols. *Jpn J Clin Oncol* 23:186–90 (1993).

Larue, J.P., Morfin, R.E. and Charles, J.F. [Zinc in the human prostate]. *J. Urol* (Paris) 91(7):463–68 (1985). Abstract Only.

Mastrogiacomo, I., Bonanni, G., Menegazzo, E., Santarossa, C., Pagani, E., Gennarelli, M., and Angelini, C. Clinical and hormonal aspects of male hypogonadism in myotonic dystrophy. *Ital J Neurol Sci* 17(1):59–65 (1996). Abstract Only.

Schaeffer, H.J. and Sirotkin, A.V. The release of insulin–like growth factor–1 by luteinized human granulosa in vitro: regulation by growth hormone, oxytocin, steroids and cAMP–dependent intracellular mechanisms. *Exp Clin Endocrinol Diabetes* 103(6):361–66 (1995). Abstract Only.

Komori, A., Yatsunami, J., Okabe, S., Abe, S., Hara, K., Suganuma, M., Kim, S.J. and Fujiki, H. Anticarcinogenic activity of green tea polyphenols. *Jpn J Clin Oncol* 23:186–90 (1993).

Tchaikovsky, V.S., Evtinova, J.V., and Basharina, O.B. [Content of steroid and androgen eceptors in skeletal muscles during adaptation to physical exercises]. *Vopr Med Khim* 31(6):80–86 (1985) [Abstract Only—p. 85].

Saden–Krehula, M., Kustrak, D., and Balzevid, N. $\Delta^4$–3–Ketosteroids in Flowers and Leaves of Vitex agnus–castus. Acta Pharm. Jugosl. vol. 41 (1991) 237–241.

Kutsky, Roman J. Testosterone. Handbook of Vitamins, Minerals and Hormones. Second Edition, Chapter 48, pp. 431–438.

Miller, Alan L. Benign Prostatic Hyperplasia. Nutritional and Botanical Therapeutic Options. Alternative Medicine Review. vol. 1, No. 1, (1996).pp. 18–25.

Ducrey, B., Marston, A., Gohring, S., Hartmann, R.W., Hostettmann, K. Inhibition of 5 α–Reductase and Aromatase by the Ellagitannins Oenothein A and Oenothenin B from Epilobium Species. Planta Medica. vol. 63, (1997) 111–114. Abstract Only.

Bassir, O. and Odebiyi, O. Male virilizing substances in some Nigerian medicinal preparations—androgenic steroids. *West Afr J Biol Appl Chem* 19:25–29 (1976).

Liang et al. Identification of $C_{19}$–androstane derivatives in natural muck by TLC. *Zhongcaoyao* 15:20–22 (1984). Abstract Only.

Dutkiewica, S. Zinc and magnesium serum levels in patients with benign prostatic hyperplasia (BPH) before and after prazosin therapy, *Mater Med Pol* 27(1):15–17 (1995).

COMPOSITIONS AND TREATMENTS FOR REDUCING POTENTIAL UNWANTED SIDE EFFECTS ASSOCIATED WITH LONG-TERM ADMINISTRATION OF ANDROGENIC TESTOSTERONE PRECURSORS

This application claims the benefit of U.S. Provisional Application Ser. No. 60/055,346, filed Aug. 11, 1997.

BACKGROUND OF THE INVENTION

A. Field of the Invention

The invention relates to the use of nutrient combinations to prevent or reduce potential adverse effects from administration of androgenic testosterone precursors to humans and other mammals Specifically, the invention relates to co-administration of androgenic testosterone precursors such as pregnenolone, androstenediols, norandrostenediols, norandrostenedione, androstenedione or dehydroepiandrosterone in combination with natural products which inhibit estrogen effects in liver, adipose, prostate, ovarian, uterine, breast and other estrogen-responsive tissues, and substances which inhibit the production of dihydrotestosterone in prostate tissue.

B. Description of Related Art

Androstenedione ($\Delta^4$-androstene-3,17-dione) is an adrenal steroid hormone. Pregnenolone is a precursor for dehydroepiandrosterone. Dehydroepiandrosterone (DHEA) is a precursor of androstenedione. Androstenedione is a direct precursor of estrone and testosterone in target tissues that possess the appropriate receptors and enzymes. Androstenediols are direct precursors for testosterone after oral administration in adult humans (unpublished data). 19-Norandrostenedione is a precursor for 19-nortestosterone, which has anabolic actions similar to testosterone, with less androgenic actions. 19-Norandrostenedione is a potential precursor for estrone. Testosterone is important for the development and maintenance of male sexual organs and characteristics, behavioral effects, anabolic (growth-promoting) actions, and metabolic effects for all tissues, especially muscles, liver and kidney. (Kutsky, R. J., *Handbook of Vitamins, Minerals and Hormones*, $2^{nd}$ ed., Van Nostrand Reinhold Company, New York, 1981). Estrogens are essential for the development and maintenance of female reproductive organs and characteristics, pregnancy, and metabolic effects for all tissues (Kutsky, 1981).

Androstenedione levels in tissues, including skeletal muscle, of men and women decrease significantly with age. (Deslypere, J. P. and Vermeulen, A., *Influence of age on steroid concentrations in skin and striated muscle in women and in cardiac muscle and lung tissue in men*, J. Clin. Endocrinol. Metab. 61:648–653 (1985)). Since muscle wasting is associated with aging, these findings suggest that the loss of androstenedione is involved in muscle wasting. The corollary that androstenedione administration would maintain muscle mass is enticing, but has not been studied yet. Nevertheless, the data support an anabolic effect of androstenedione on muscle tissue in both men and women, with more effectiveness in men.

Blood levels of androstenedione decrease in some young men during prolonged, intense exercise. This decrease is thought to impede performance improvements. For example, serum androstenedione levels declined as weightlifting intensity increased in young men. (Alen et al., *Responses of serum androgenic-anabolic and catabolic hormones to prolonged strength training*, Int. J Sports Med. 9:229–233 (1988)). While androstenedione and other androgens were decreased, serum testosterone was maintained, which suggests that androstenedione provides precursors for synthesis of testosterone by muscle. Other indicators of over-training were more apparent as androstenedione levels decreased. Thus, androstenedione supplementation to young men engaged in vigorous weight training may help prevent androstenedione deficiency, and maintain anabolic responses to weight training.

To counteract this decrease in androstenedione levels, athletes have taken androstenedione orally, nasally or intravenously to increase testosterone levels. Empirical research supports the link between the administration of androstenedione and increases in testosterone levels. For example, oral and nasal administration of androstenedione to women increases serum testosterone levels. (Maresh, V. B. and Greenblatt, R. B., *The in vivo conversion of dehydroepiandrosterone and androstenedione to testosterone in the human*. Acta Endocrinol. 41:400–406 (1962); Mattern, C. and Hacker, R., European Patent Application No. 97-13 0639077 (1977)). Furthermore, androstenedione is converted into testosterone in muscle and adipose tissue in humans after intravenous administration. (Belisle et al, *Metabolism of androstenedione in human pregnancy: use of constant infusion of unlabeled steroid to assess its metabolic clearance rate, its production rate, and its conversion into androgens and estrogens*, Am. J. Obstet. Gynecol. 136:1030–1035 (1980); Longcope, C. and Fineberg, S. E., *Production and metabolism of dihydrotestosterone in peripheral tissues*, J. Steroid Biochem. 23:415–419 (1985)). (This reference, and all the other references in this and subsequent sections, are incorporated by reference in their entirety.) These data have generated interest in androgenic testosterone precursors as ergogenic aids for improving anabolism in exercising persons, especially weight lifters and bodybuilders. Dietary supplement products containing androstenedione, androstenediols, norandrostenedione and norandrostenediols alone or in combination with other ingredients have appeared on the market recently.

Evidence has accumulated that suggests androstenedione excess is not benign. Androstenedione affects hormonally responsive target tissue in males and females. Androstenedione administration may cause overproduction of estradiol from estrone, and dihydrotestosterone (DHT) from testosterone. Estradiol and DHT account for most of the hormonal effects of estrogens and testosterone in target tissues. For example, long-term treatment of dogs and monkeys with androstenedione causes prostate enlargement and temporary shrinkage of testicles. While dogs are more sensitive to estrogens than humans, side effects may also occur in humans. Such side effects may include breast and prostatic cancer, benign prostatic hyperplasia, and hirsutism or acne in women. Since DHEA is a metabolic precursor of androstenedione, DHEA administration may also be associated with harmful side effects. Thus, androstenedione and DHEA administration should be carefully monitored to provide the desired anabolic effects without causing harmful side effects.

There is insufficient evidence to assess side effects from norandrostenediols or norandrostenedione from animal or human scientific literature. However, the known metabolic pathways of these prohormones indicate that estrone, in amounts equivalent to those formed by androstenedione or testosterone, can be formed from nor- analogs of androstenedione and testosterone (Raeside, J. I., Renaud, R. L., and Friendship, R. M., *Aromatization of 19-norandrogens by porcine Leydig cells*. J Steroid Biochem. 32(5):729–735

(1989)). These results indicate that the potential for unwanted side effects with nor-prohormones may be equivalent to that for androstenedione and testosterone.

Thus, there is a need for a composition and method for minimizing or preventing unwanted side effects associated with the administration of androgenic testosterone precursors in humans. In particular, there is a need for a composition and method which maintains androgenic testosterone precursor levels while minimizing or eliminating the effects of estrogen and DHT excess.

SUMMARY AND OBJECTS OF THE INVENTION

The present invention provides a safe and effective composition of, and method for administering, androgenic testosterone precursors which promote anabolic metabolism while inhibiting unwanted side effects Those side effects result from the metabolism of prohormones into byproducts which cause such side effects. The present invention combines novel ingredients to limit the effects of these metabolic byproducts without interfering with the beneficial effects of androgenic testosterone precursor administration. Specifically, the invented composition includes components which reduce or prevent the unwanted side effects of androgenic testosterone precursor administration in hormone responsive-tissues without inhibiting anabolic effects in muscle.

The composition of the present invention includes androgenic testosterone precursors such as pregnenolone, androstenedione, dehydroepiandrosterone (DHEA), androstenediols, norandrostenedione, and/or norandrostenediols in combination with one or more natural products for inhibiting estrogen effects in liver, adipose, prostate, ovarian, uterine, breast and other tissues responsive to estrogen (hereafter "anti-estrogen activity"). The composition further includes one or more substances for preventing the production of dihydrotestosterone (DHT) in prostate tissue (hereafter "anti-DHT activity").

Natural products with anti-estrogen activity include catechin polyphenols, tocotrienols, isoflavones and similar flavonoid compounds such as citrus flavonoids and saponin flavones, phytosterols, resorcyclic acid lactones, indoles, saponins, glucarates and guaianolides from Asteraceae species. Substances with anti-DHT-activity include zinc salts, Saw Palmetto berry (*Serenoa repens*), Pygeum africanum, and green tea (*Camellia sinensis*). Natural products with anti-estrogen activity and substances with anti-DHT activity may further include whole herbs or plants, parts thereof, powders thereof, and semi-purified extracts as well as purified extracts.

It is an object of the present invention to provide a composition of, and method for administering, androgenic testosterone precursor(s) which promotes anabolic responses during exercise while minimizing unwanted side effects.

It is another object of the present invention to provide a composition of, and method for administering, androgenic testosterone precursor(s) and a natural product(s) which promote anabolic responses to exercise while inhibiting estrogen effects in the liver, adipose, prostate, ovarian, uterine, breast and other tissues responsive to estrogen.

It is a further object of the present invention to provide a composition of, and method for administering, androgenic testosterone precursor(s) and a substance(s) with an anti-DHT activity to promote anabolic responses during exercise while inhibiting unwanted side effects caused by the overproduction of DHT from testosterone.

It is still another object of the present invention to provide a composition of, and method for administering, androgenic testosterone precursor(s) which prevents overdosing of androgenic testosterone precursors.

It is still another object of the present invention to provide a composition of, and method for administering, androgenic testosterone precursor(s) which promotes anabolic metabolism while maintaining androgenic testosterone precursors, testosterone, DHT, DHEA sulfate and other hormones within normal physiological ranges.

It is a further object of the invention to provide a composition of, and method for, administering androgenic testosterone precursors which spares normal hormones levels from depletion due to overtraining.

These and other objects, features and advantages of the invention will be clear to a person of ordinary skill in the art upon reading this specification in light of the appending drawing.

DETAILED DESCRIPTION OF THE PREFERRED EMBODIMENT

Figure 1:
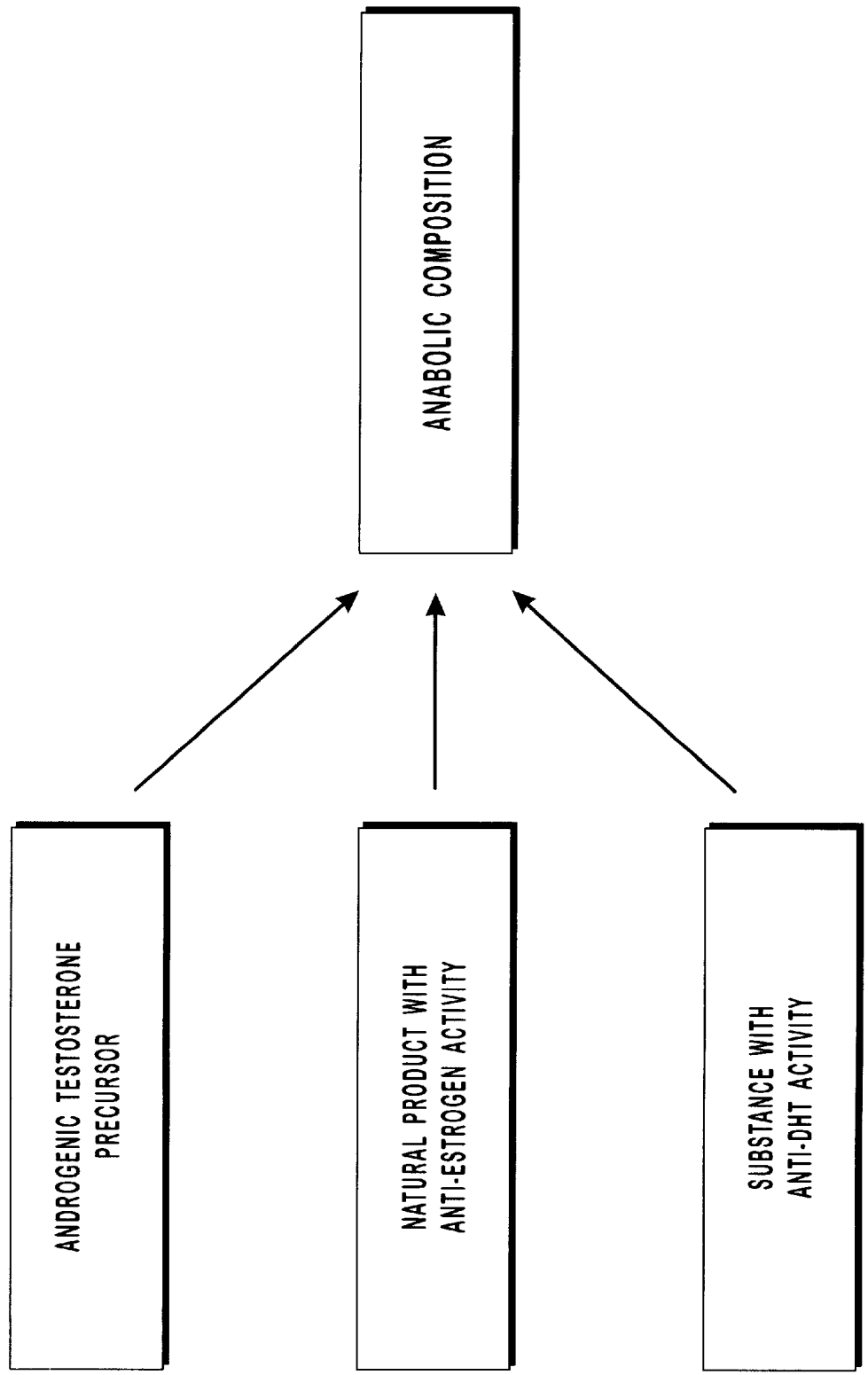
FIG. 1 depicts the components of the present invention.

Referring to FIG. 1, the invented composition is intended to be taken as an oral dosage form. The invented composition includes at least one androgenic testosterone precursor such as pregnenolone, androstenedione, DHEA, androstenediols, norandrostenedione, norandrostenediols, and analogs thereof, in combination with one or more natural products having an anti-estrogen activity and one or more substances having an anti-DHT activity. The ingredients of the present invention lend themselves to the incorporation into, and the production of, nutritional supplements which are especially useful as orally-administrable dosage forms including, but not limited to, capsules, tablets, bars, gums, candies, powders, drinks, liquid sprays and liposomal solutions (hereafter "oral dosage forms").

A. Description of the Ingredients

Androgenic Testosterone Precursors—The invented composition includes metabolic precursors of estrogen and testosterone such as pregnenolone, androstenedione ($\Delta^4$-androstene- 3,17-dione), dehydroepiandrosterone (DHEA), $\Delta^4$-androstene-3$\beta$,17$\beta$-diol (4-androstenediol), $\Delta^5$-androstene-3$\beta$,17$\beta$-diol (5-androstenediol), 19-norandrost-4-ene-3,17-dione (19-norandrostene-dione), and 19-norandrost-4 or 5-ene-3$\beta$,17$\beta$-diol (norandrostenediols). Analogs of these androgenic testosterone precursors which are estrogen or testosterone precursors are also within the scope of the present invention. These androgenic testosterone precursors are available from commercial sources such as Technical Sourcing International, Inc. and Sigma Aldrich Fine Chemicals. Methods of preparing androstenedione and its analogs are disclosed in U.S. Pat. Nos. 4,100,026, 4,100,027, 4,474,701, 5,418,145, and 5,516,649. Each of these patents is incorporated by reference in its entirety.

Natural products containing anti-estrogen activity—The natural products with an anti-estrogen activity reduce or inhibit estrogen effects in estrogen-responsive tissues. Such natural products act by blocking estrogen receptors in estrogen-responsive tissues or by effecting the removal and/or destruction of estrogen in the body. Estrogen-responsive tissues include liver, adipose, prostate, ovarian, uterine, and breast tissues.

The natural products may include, but are not limited to, catechin polyphenols, tocotrienols, isoflavones and similar flavonoid compounds such as citrus flavonoids and saponin flavones, phytosterols, resorcyclic acid lactones, indoles, saponins, glucarates and guaianolides from Asteraceae species. For example, catechin polyphenols, bioflavonoids, indoles and saponins in green tea, soy and other plants are effective in blocking estrogen receptors in prostate tissue. Glucarates, tocotrienols and indole-3-carbinol stimulate the removal of estrogen from the body. Biochanin A and 7,8-benzoflavone are effective in blocking estrogen receptor-binding sites and reducing aromatase activity. Guaianolides from Asteraceae species also inhibit aromatase activity.

Herbs and plants, and extracts therefrom, which have such anti-estrogen activity, are also within the scope of the invention. Natural products containing catechin polyphenols include green tea, black tea and catechu. Preferred natural products containing tocotrienols include rice bran, rice bran oil, and red palm oil. The preferred sources of isoflavones and bioflavonoids include soybeans, pulses, soy germ, bee propolis, alfalfa, cloves, and citrus fruits such as oranges. Other flavonoid-rich herbs, plants, foodstuffs and purified compounds from flavonoid-rich herbs, plants and foodstuffs are also within the scope of the present invention. Preferred sources of phytosterols include alfalfa, soy extracts and red clover. Preferred sources of indoles include broccoli extracts and synthetic sources. Finally, the preferred sources of saponins include soy.

The preferred glucarates include calcium-D-glucarate, potassium hydrogen D-glucarate, glucaric acid, D-glucaro-1,4-lactone and pharmaceutically-acceptable salts thereof.

Other natural products are within the scope of the present invention if they are effective in blocking the binding of estrogen to estrogen receptors, or in increasing the removal or destruction of estrogen in the body without inhibiting the estrogenic pathway in muscle. Assays to measure such activity are well-known to those of skill in the art. For example, receptor binding assays may be conducted according to the method of J. L. Witliff and E. D. Savlov (*Estrogen-binding capacity of cytoplasmic forms of the estrogen receptors in human breast cancer*, in Estrogen Receptors in Human Breast Cancer, W. L. McGuire, P. P. Carbone and E. P. Vollmer, eds, Raven Press, New York (1975), pp.73–86), which is incorporated by reference herein. Briefly, extracts are prepared from frozen tissue samples (e.g., breast tissue) by immersion in liquid nitrogen, and then shattered to form a powder. The powder is homogenized in ice cold 10 mM Tris-HCl, 1.5 mM EDTA, 250 mM sucrose, pH 7.4, to form the extract. Protein concentrations may be adjusted according to standard methods.

The inhibition of estrogen-receptor binding may be measured by sucrose gradient assay, as disclosed in Witliff and Savlov (1975). Briefly, tissue aliquots, which are prepared as described above, are incubated with radiolabeled estrogen and varying amounts of a natural product or extract therefrom. After incubation is complete, the amount of radiolabeled estrogen is determined in control and experimental samples after separation of the free estrogen from bound estrogen. To separate free from bound estrogen, the incubation mixture is mixed with dextran-coated charcoal, centrifuged at 1,000×g for 10 minutes at 3° C. and then further centrifuged on a linear sucrose gradient (5–40%) for 15–17 hours at about 308,000×g. After centrifugation, each gradient is fractionated and the amount of radioactivity in each fraction determined with a scintillation counter. The dextran-coated charcoal procedure of Wittliff and Savlov (1975) is an alternate procedure for the determination of estrogen receptor binding. Another preferred assay for estrogen-receptor binding is the luciferase whole cell assay described in Lobaccaro et al. (*Steroidal affinity labels of the estrogen receptor. 3. Estradiol* 11β-*n-alkyl derivatives bearing a terminal electrophilic group: Anti-estrogenic and cytotoxic properties, J. Med. Chem.* 40:2217–27 (1997)), which is incorporated herein by reference.

To identify natural products which affect the removal or destruction of estrogen from the body, blood serum assays may be used. For example, a radiolabeled estrogen is infused into a subject mammal followed by the infusion of unlabeled androstenedione. Whole blood samples are periodically withdrawn and the metabolic clearance rate of the infused radiolabeled estrogen is measured. By comparing the clearance rates in control and experimental subjects provided with natural products, the efficacy of those products may be readily determined. An example of a metabolic clearance rate determination for androstenedione, DHEA, testosterone, estrone and estradiol is disclosed in Belisle et al. (*The metabolism of androstenedione in human pregnancy; The use of constant infusion of unlabeled steroid to assess its metabolic clearance rate, its production rate, and its conversion to androgens and estrogens, Am. J Obstet. Gynecol.*, 136: 1030–1035 (1980)), which is incorporation by reference herein. Anti-estrone antibodies are available from Steran Research Ltd. (London, England). The quantitation of androstenedione and estrogen levels in serum have been performed by RIA, as described in Resko et al. (*Sex steroids in the umbilical circulation of fetal rhesus monkeys from the time of gonadal differentiation, J. Clin. Endocrinol. Metab* 50:900–905 (1980)), and Belisle et al. (*The effect of constant infusion of unlabeled dehydroepiandrosterone sulfate on maternal plasma androgens and estrogens, J. Clin. Endocrinol. Metab.* 45:544–550 (1977)), which are incorporated by reference herein. Methods for radioactive, enzymatic and colorimetric quantitation of antigen levels are generally disclosed in Harlow, E. and Lane, D., Antibodies: A Laboratory Manual (Cold Spring Harbor, 1988), which is incorporated by reference herein.

Substance with anti-DHT activity—The substance with anti-DHT activity inhibits the conversion of testosterone to dihydrotestosterone. Substances having anti-DHT activity include zinc salts such as the acetate, alaninate, alpha-aminobutyrate, arginate, ascorbate, benzoate, butyrate, beta-hydroxybutyrate, n-butyrate, carnosinate, chloride, citrate, formate, glycinate, gluconate, histidinate, iso-leucinate, iso-valinate, leucinate, lysinate, monomethionate, oxide, picolinate, propionate, succinate, sulfate, transferrin, and valinate forms. The zinc salt is preferably a pharmaceutically acceptable form, as will be appreciated by those of skill in the art. Other substances with anti-DHT activity include Saw palmetto berry (*Serenoa repens*) powders and extracts, *Pygeum africanum* powders and extracts, green tea powders and extracts containing epicatechin gallete esters, pumpkin seeds oils and powders, beta-sitosterol, and calcium-D-glucarate. In a more preferred embodiment of the invention, the substance with anti-DHT activity is a zinc salt, including but not limited to, zinc arginate, citrate, acetate, chloride, sulfate, picolinate, oxide and monomethionate.

The ability of substances to inhibit DHT production may be conveniently determined by measuring the conversion of radiolabeled testosterone to DHT in cell extracts or tissue homogenates. Such assays are preferably conducted using extracts from prostate tissue or from prostate tissue culture cells. The preparation of tissue homogenates and the measurement of the conversion of radiolabeled testosterone to DHT are described in articles by J. P. Deslypere and A.

Vermeulen (*Influence of age on steroid concentration in skin and striated muscle in women and in cardiac muscle and lung tissue in men, J. Clin. Endocrinology Metab.* 61: 648–53 (1985)), J. P. Deslypere and A. Vermeulen (*Aging and tissue androgens, J. Clin. Endocrinology Metab.* 53: 430–34 (1981)) and J. P. Deslypere et al. (*Androgen concentrations in sexual and non-sexual skin as well as in striated muscle in man, J. Steroid Biochem.* 13: 1455–58 (1980)), which are incorporated by reference herein for the disclosed methodologies. Steroids are extracted from the homogenates by precipitation of the protein with acetone, the acetone is evaporated from the aqueous phase, the aqueous phase is extracted with ether and the residue defatted with 70% methanol. After evaporation of the methanol, the aqueous phase is extracted with dichloromethane. Testosterone and DHT are separated by paper chromatography in a Bush B3 system. To further separate testosterone from other comigrating compounds such as androstenedione, the products may be separated by column chromatography using Sephadex LH20. DHT may be further separated from androstenedione by thin layer chromatography on an $Al_2O_3$ support with a 3:1:1 (v/v) benzene/chloroform/ethylacetate system. RIA procedures have been described in Deslypere and Vermeulen (1981) and Deslypere et al. (1980), which are incorporated by reference for the disclosed procedures and sources of antibody.

B. Composition of the Invention

The ingredients of the invention are readily available commercially or may be synthesized according to known methods. The androgenic testosterone precursors, natural products with anti-estrogen activity, and substances with anti-DHT activity are preferably of food-grade quality or better. Pharmaceutically-acceptable salts of these ingredients are also within the scope of the present invention. When amounts are specified as weight percentages, those percentages are based on the total weight of androgenic testosterone precursor, natural product with anti-estrogen activity, and substance with anti-DHT activity.

For androstenedione, the therapeutically effective dosage level can range from about 1 mg to about 1,000 milligrams per day. In a more preferred embodiment, the effective dosage ranges from about 25 to about 250 milligrams per day. In the most preferred embodiment of the invention, the dosage is about 100 milligrams per day. These dosages are for persons within a weight range of about 50 to about 110 kilograms. These ranges may proportionately adjusted for persons or greater of lesser weights. For androstenedione analogs, the effective dosage is determined by normalizing the analog's activity to that of androstenedione.

For DHEA, the therapeutically effective dosage level can range from about 1 mg to about 1600 milligrams per day. In a more preferred embodiment, the effective dosage ranges from about 5 to about 100 milligrams per day. In the most preferred embodiment of the invention, the dosage is about 25 milligrams per day. In another preferred embodiment, the DHEA dosage is in excess of 30 milligrams per day. As for androstenedione, these dosage ranges may be proportionally adjusted for persons outside the weight range of about 50 to about 110 kilograms. For DHEA analogs, the effective dosage is determined by normalizing the analog's activity to that of DHEA.

For androstenediols, the therapeutically effective dosage level can range from about 1 mg to about 1500 milligrams per day. In a more preferred embodiment, the effective dosage ranges from about 5 to about 150 milligrams per day. In another more preferred embodiment, the effective dosage ranges from greater than 30 to about 150 milligrams per day. In the most preferred embodiment of the invention, the dosage is about 100 milligrams per day. As for androstenedione, these dosage ranges may be proportionally adjusted for persons outside the weight range of about 50 to about 110 kilograms. For androstenediol analogs, the effective dosage is determined by normalizing the analog's activity to that of androstenediol.

For pregnenolone, norandrostenediols and norandrostenedione, the therapeutically effective dosages can range from about 1 mg to about 1000 milligrams per day. In a more preferred embodiment, the effective dosages may range from about 5 to about 150 milligrams per day. In the most preferred embodiment, the amount of pregnenolone is about 100 milligrams per day. These dosage ranges may be proportionally adjusted for persons outside the weight range of about 50 to about 110 kilograms. For analogs of pregnenolone, norandrostenediols, and norandrostenedione, the effective dosage is determined by normalizing the analog's activity to that of pregnenolone, the norandrostenediol or norandrostenedione, respectively.

The therapeutically effective dosage range for the purified or partially purified natural product(s) with anti-estrogen activity may range from about 1 to about 75 weight percent. In a more preferred embodiment of the invention, the effective range is from about 10 to about 50 weight percent. In the most preferred embodiment, the effective dosage is about 20 weight percent. For crude extracts or herb or plant parts, the effective dosage levels may range from about 10 to about 70 weight percent. In a more preferred embodiment, the effective dosage levels may range from about 20 to about 50 weight percent. In the most preferred embodiment, the effective dosage is about 30 weight percent.

The therapeutically effective dosage range of the substance with anti-DHT activity is from about 1 to about 75 weight percent. In a more preferred embodiment, the effective dosage amount may range from about 10 to about 50 weight percent. In the most preferred embodiment, the amount is about 20 weight percent.

When the substance with anti-DHT activity is zinc, the effective dosage range of elemental zinc may range from about 1 to about 250 mg. In a more preferred embodiment, the effective dosage ranges from about 5 to about 150 milligrams. In the most preferred embodiment, the amount of anti-DHT activity is about 10 mg. For zinc salts, the effective ranges may be calculated by normalizing the amount of zinc in the zinc salt to that of elemental zinc.

In a more preferred embodiment of the invention for women, the substance with anti-DHT activity may be omitted from the composition. In such a composition for women, the relative amounts of androgenic testosterone precursor and natural product with anti-estrogen activity are as disclosed above, except that the relative weight percentages are based on the total weight of androgenic testosterone precursor and natural product with anti-estrogen activity.

The present invention may further include flavorings and colorings to increase consumer appeal and to mask any unpleasant tastes of the composition. This is particularly true for androstenedione, which has a bitter taste.

The present invention may beneficially also be admixed with various pharmaceutically suitable, inactive excipients, carriers, diluents, lubricants and adjuvants and then formed into capsules and tablets, as will be appreciated by those of ordinary skill in the art. Examples of inactive excipients, carriers, diluents, lubricants, disintegrants include, but are not limited to, the following: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicon dioxide (silica), food glaze, talc, croscarmellose sodium, povidone, water and gelatin. Additional inactive excipients, carriers, diluents, lubricants and adjuvants which may be used with the invented composition are disclosed in the Handbook of Food Additives (CRC Press), which is incorporated by reference herein in relevant part. (Pharmaceutically suitable, inactive excipients, carriers, diluents, lubricants, adjuvants and disintegrants are hereafter termed "pharmaceutically suitable carriers.")

For capsules or tablets, the amount of the composition per oral dosage may be varied according to the preferred size of the capsule or tablet. For capsules, the total amount of the composition may range from about 1 mg to about 2000 mg, although greater or lesser amounts are within the scope of the invention. For tablets, the total amount of composition may range from about 10 mg to about 2000 milligrams, although greater or lesser amounts are within the scope of the invention. For bars, gums, candies, sprays, powders and drinks, the invented composition may be mixed with inactive ingredients, colorings and flavorings to achieve the preferred dosage, as will be appreciated by those of skill in the art.

C. Method of Making Oral Dosage Forms

The invented composition is intended to be taken orally. In addition to tablets and capsules, other equivalent oral dosage forms are within the scope of the invention, as will be readily appreciated by those of skill in the art. Methods of forming capsules, tablets and powders by wet or dry granulation, are well-known in the art. Suitable procedures for making oral dosage forms are described in Pharmaceutical Dosage Forms and Drug Delivery Systems, $6^{th}$ Ed. (H. C. Ansel, N. G. Popovich and L. V. Allen, Eds., Williams & Wilkins (1995)), which is incorporated by reference herein. Other suitable procedures are disclosed in Pharmaceutical Dosage Forms: Disperse Systems, Vol. 2, $2^{nd}$ Ed. (H. A. Lieberman, L. Lachman and J. B. Schwartz, Eds. (1996)), and Pharmaceutical Dosage Forms: Tablets, Vols. 2 and 3, $2^{nd}$ Ed. (H. A. Lieberman, L. Lachman and J. B. Schwartz (1990)), which are incorporated by reference herein. In the most preferred embodiment of the invention, the composition is manufactured according to good manufacturing practices, as disclosed in 21 C.F.R., part 110 and quality tested according to US Pharmacopia, $23^{rd}$ Ed., both of which are incorporated by reference herein.

D. Method of Using the Invented Composition

The composition of the present invention may be taken one or more times per day. In the most preferred embodiment of the invention, the recommended dosage of androstenedione and DHEA should preferably not exceed 150 and 250 milligrams per day, respectively, to avoid potentially harmful side effects. If more than one dosage per day is desirable, then the composition may be mixed with inert ingredients and divided into the desired number of proportionate doses, as will be appreciated by those of skill in the art.

In the most preferred embodiment of the present invention, the anti-DHT activity includes a zinc salt. Zinc salts act as an emetic above certain dosage levels. For example, dosages of zinc sulfate above about 150 milligrams per day cause emesis. Thus, taking an overdose of androgenic testosterone precursors may be prevented through controlling zinc levels in the invented composition, as will be appreciated by those of skill in the art. For example, if the invented composition is calibrated at one dosage per day, the zinc levels in each dose may be adjusted such that a person taking multiple doses per day will ingest sufficient zinc to trigger an emetic response and cause expulsion of the overdose.

E. Examples of Compositions

The following examples will include embodiments within the scope of the invention, although the invention is not intended to be limited by or to these embodiments. These examples illustrate preferred modes of administering the invention as contemplated by the inventor.

| Example 1: | androstenedione | 100 mg |
| --- | --- | --- |
| | green tea extract | 50 mg |
| | (20% polyphenols) | |
| | zinc (as arginate) | 10 mg |
| Example 2: | androstenedione | 100 mg |
| | green tea extract | 50 mg |
| | (20% polyphenols) | |
| | copper | 0.5 mg |
| | zinc (as arginate) | 10 mg |
| Example 3: | androstenedione | 100 mg |
| | chrysin | 50 mg |
| | zinc (as monomethionate) | 25 mg |
| Example 4: | androstenedione | 50 mg |
| | Biochanin A | 50 mg |
| | soy isoflavones (12%) | 200 mg |
| Example 5: | androstenedione | 50 mg |
| | Red clover (Trifolium pratense) | 200 mg |
| | Saw Palmetto berry standardized extract | 60 mg |
| Example 6: | DHEA | 25 mg |
| | Green tea extract | 50 mg |
| | (60% polyphenols) | |
| | Pygeum africanum | 100 mg |
| Example 7: | androstenedione | 100 mg |
| | zinc (as amino acid chelate) | 15 mg |
| | Saw Palmetto berry standardized extract | 50 mg |
| Example 8: | androstenedione | 100 mg |
| | beta-sitosterol | 200 mg |
| | zinc (as amino acid chelate) | 15 mg |
| Example 9: | androstenedione | 100 mg |
| | tocotrienols (rice bran oil) | 150 mg |
| | zinc (as amino acid chelate) | 10 mg |
| Example 10: | androstenedione | 100 mg |
| | Pygeum africanum | 150 mg |
| | zinc (as amino acid chelate) | 10 mg |
| Example 11: | androstenedione | 100 mg |
| | citrus bioflavonoids | 500 mg |
| | isoflavone | 100 mg |
| Example 12: | androstenedione | 100 mg |
| | Genistein | 20 mg |
| | Green tea extract | 200 mg |
| | (80% polyphenols) | |
| Example 13: | androstenedione | 100 mg |
| | Alfalfa (Medicago satira) | 500 mg |
| | Green tea extract | 200 mg |
| | (20% polyphenols) | |
| Example 14: | androstenedione | 100 mg |
| | Green tea extract | 100 mg |
| | (80% polyphenols) | |
| | Saw Palmetto berry extract | 60 mg |
| | zinc (as arginate) | 10 mg |
| Example 15: | androstenedione | 100 mg |
| | beta Sitosterol | 100 mg |
| | Green tea extract | 100 mg |
| | (80% polyphenols) | |
| | Saw Palmetto berry extract | 60 mg |
| | Pygeum africanum | 50 mg |
| | zinc (as arginate) | 10 mg |

| | | | |
|---|---|---|---|
| | | -continued | |
| Example 16: | androstenedione | 100 | mg |
| | soy saponin | 50 | mg |
| | Green tea extract (20%) | 100 | mg |
| Example 17: | androstenedione | 100 | mg |
| | indole-3-carbinol | 3 | mg |
| | zinc (as arginate) | 10 | mg |
| Example 18: | DHEA | 25 | mg |
| | indole-3-carbinol | 3 | mg |
| | zinc (as arginate) | 10 | mg |
| Example 19: | androstenedione | 100 | mg |
| | Green tea extract (20%) | 100 | mg |
| | zinc (as arginate) | 10 | mg |
| | calcium D-glucarate | 500 | mg |
| Example 20: | androstenedione | 100 | mg |
| | indole-3-carbinol | 3 | mg |
| | calcium D-glucarate | 500 | mg |
| Example 21: | androstenedione | 50 | mg |
| | chrysin | 100 | mg |
| | Hesperidin | 100 | mg |
| Example 22: | androstenedione | 50 | mg |
| | soy isoflavones | 25 | mg |
| | zearalenone | 10 | mg |
| Example 23: | Androstenedione | 100 | mg |
| | Red clover (*Trifolium pratense*) | 250 | mg |
| | Green tea extract (20%) | 100 | mg |
| Example 24: | androstenedione | 100 | mg |
| | alfalfa (coumesterol) | 250 | mg |
| | zinc (monomethionate) | 25 | mg |
| Example 25: | DHEA | 25 | mg |
| | androstenedione | 50 | mg |
| | chrysin | 50 | mg |
| | Green tea extract (20% polyphenols) | 200 | mg |
| | zinc (as arginate) | 10 | mg |
| Example 26: | androstenedione | 100 | mg |
| | Red clover | 200 | mg |
| | alfalfa | 100 | mg |
| | soy germ | 200 | mg |
| | citrus bioflavonoids | 50 | mg |
| | Green tea extract (20% polyphenols) | 200 | mg |
| Example 27: | androstenedione | 100 | mg |
| | formononetin | 25 | mg |
| | Saw palmetto berry extract | 60 | mg |
| Example 28: | 4-androstenediol | 100 | mg |
| | green tea extract (20% polyphenols) | 50 | mg |
| | copper (as lysinate) | 0.5 | mg |
| | zinc (as monomethionate) | 10 | mg |
| Example 29: | 5-androstenediol | 100 | mg |
| | green tea extract (20% polyphenols) | 50 | mg |
| | copper (as lysinate) | 0.5 | mg |
| | zinc (as monomethionate) | 10 | mg |
| Example 30: | 19-norandrostenedione | 100 | mg |
| | Red Clover (*Trifolium pratense*) | 500 | mg |
| | *Pygeum africanum* extract | 200 | mg |
| Example 31: | pregnenolone | 100 | mg |
| | Ipriflavone | 250 | mg |
| | Pumpkin seed powder | 200 | mg |
| Example 32: | pregnenolone | 100 | mg |
| | 19-norandrost-4-enediol | 50 | mg |
| | Genistein (>90%) | 40 | mg |
| | beta-Sitosterol | 500 | mg |
| Example 33: | pregnenolone | 10 | mg |
| | DHEA | 25 | mg |
| | androstenedione | 50 | mg |
| | 4-androstenediol | 25 | mg |
| | 19-norandrostenedione | 25 | mg |
| | 19-norandrost-4-enediol | 50 | mg |
| | Green tea extract (90% polyphenols) | 200 | mg |
| | Calcium D-glucarate | 500 | mg |
| | Zinc (as gluconate) | 10 | mg |

Suitable amounts of other natural products with anti-estrogen activity will include Alfalfa (*Medicago sativa*) (50–500 mg)
Bee propolis (50–200 mg)
7,8-Benzoflavones (10–50 mg)
Biochanin A (10–50 mg)
Broccoli extract (w/ sulforophane—50–500 mg)
Calcium D-glucarate (200–500 mg)
Chrysin (10–200 mg)
Citrus bioflavonoids (50–2000 mg)
Coumestrol (5–40 mg)
Daidzein (>90%–5–40 mg)
Enterolactone (5–40 mg)
Equol (5–40 mg)
Flavone (>90%–5–40 mg)
Formononetin (>90%–5–40 mg)
Genistein (>90%–5–40 mg)
Glycetin (5–40 mg)
Green tea extract
  (20% polyphenols—50–200 mg;
  40% polyphenols—40–100 mg;
  60% polyphenols—25–100 mg;
  80% polyphenols—20–100 mg;
  90% polyphenols—10–100 mg)
Green tea powder (100–500 mg)
Hesperidin (50–200 mg)
Indole-3-carbinol (1–5 mg)
Ipriflavone (50–250 mg)
Naringer (50–100 mg)
Naringenin (50–250 mg)
Red Clover (Trifoliumpratense) (50–500 mg)
Red palm oil (100–1000 mg)
Rice bran oil (100–1000 mg)
Orange juice solids (0.5–50 g)
Phloretin (>90%—5–40 mg)
Quercetin (50–100 mg)
beta-Sitosterol (50–200 mg)
Soy isoflavones (2% in soy germ—100–500 mg; 12% in soy germ—50–200 mg)
Soy saponin (50–250 mg)
Tocotrienols (40%—100–500 mg) (e.g. rice bran oil)
Tocotrienols (100–500 mg) (e.g. red palm oil)
Tribulus terrestris (e.g., Tribestan®)) extracts (10–1000 mg)
Zearalenol (5–40 mg)
Zearalenone (5–40 mg)
Zearalone (5–40 mg)

Suitable amounts of other substances with anti-DHT activity will include:

Calcium D-glucarate (500 mg)
Green tea extract (20%—50–200 mg; 40%—40–150 mg; 60%—25–100 mg; 80%—20–100 mg; 90%—10–100 mg)
Green tea powder (100–500 mg)
Pumpkin seed oil (100–500 mg)
Pumpkin seed powder (100–500 mg)
Pygeum africanum extract (50–200 mg)
Pygeum africanum powder (100–500 mg)
Saw palmetto berry extract (standardized to sterols—50–200 mg)
Saw palmetto berry extract (standardized to fatty acids—50–200 mg)
Saw palmetto berry powder (100–500 mg)

beta-Sitosterol (50–500 mg)

Tribulus terrestris (e.g., Tribestan®) extracts (10–1000 mg)

Zinc salts (5–50 mg of elemental zinc)

F. Human Experimental Data Using the Present Invention:

An example of the present invention (see Exemplary Composition #2) was tested in a single adult human male, aged 41 years, who had an eight month history of resistance training, and was taking 25 mg of DHEA per day for 15 months prior to start of the experiment. The subject was tested for baseline levels in serum of the following hormones: total testosterone, free testosterone, percentage (%) free testosterone, DHEA, DHEA-sulfate, androstenedione, 3-alpha-androstanediol glucuronide, and total estrogens Previous testing for total testosterone five months prior to baseline testing showed that DHEA supplementation at 25 mg per day for long time periods prior to the study period did not affect testosterone levels, indicating a steady state was reached for DHEA effects. The subject then took, as daily doses from an oral dietary supplement, 100 mg androstenedione, 50 mg green tea extract (20% polyphenols), 10 mg zinc (as arginate), and 0.5 mg copper (as lysinate). The subject also ingested 50 mg of supplemental zinc (as gluconate) daily, which was a continuation of previous practices, and continued to take 25 mg of DHEA daily. The subject continued regular diet, supplementation, and exercise habits for 4.5 months, after which another set of hormone levels was measured.

The results are listed in the Table below. Initially, levels of each hormone measured were in the lower part of the reference ranges, consistent with the results of Alen, et al., 1988, indicating an overtraining syndrome. Free testosterone levels were below the reference range, in spite of consistent supplementation with DHEA. It can be seen that androstenedione supplementation was associated with increased levels of total testosterone, free testosterone, DHEA, DHEA-sulfate, androstenedione, 3-alpha-andtrostanediol glucuronide, and estrogens. Hormone levels, which prior to androstenedione supplementation were approaching deficient levels, were increased into safe levels at the middle or upper parts of reference ranges, i.e., a desired result. It can be seen that no hormone was elevated above the reference range, which would indicate a risk of side effects from testosterone and estrogen metabolites. Also desirable was the large percentage change for the chief androgen metabolite, 3-alpha-androstanediol glucuronide, indicating a healthy metabolic conversion of excess androgens to safe metabolites.

The large increase in DHEA sulfate levels suggested that less DHEA was being used to provide androgenic hormones, and thus, DHEA sulfate levels rose to healthier levels. DHEA has important roles on its own for immune system modulation, brain function, and anticatabolic actions. In other words, androstenedione supplementation induced a DHEA-sparing action. In summary, the results showed safe increases of desired hormones, with no abnormally high levels of unwanted hormones, such as total estrogens. These results suggest that the exemplary composition of the present invention was successful in preventing unwanted side effects from long-term administration of androgenic testosterone precursors.

In addition, the subject reported no side effects associated with androgenic or estrogenic actions. There was no reported or observable changes in acne, hirsutism, or prostate function. The subject did report an increase in body weight of 3 kg, along with large increases in strength, as exemplified by increases in pounds lifted in all weightlifting exercises. Thus, the claimed invention was associated with safe increases in androgenic hormone levels that most likely led to gains in muscle mass.

TABLE

Serum Hormone Levels Before and After Long-Term Supplementation with Androgenic Testosterone Precursors to Reduce Unwanted Side Effects

| Hormone | Reference Range | Time 0 | Time 4.5 months | % Change |
|---|---|---|---|---|
| Testosterone, total | 241–830 ng/dl | 291 | 401 | +37.8 |
| Testosterone, free | 13–40 pg/ml | 12.3 | 14.7 | +19.5 |
| % Free testosterone | 0.2–0.7% | 0.42 | 0.37 | −11.9 |
| Androstenedione | 50–250 ng/dl | 71 | 129 | +45.0 |
| DHEA | 1.4–12.5 ng/ml | 3.3 | 5.2 | +57.6 |
| DHEA sulfate | 59–452 mcg/dl | 152 | 404 | +166 |
| 3-α-Androstanediol glucuronide | 260–1500 ng/dl | 262 | 692 | +164 |
| Estrogens | 40–115 pg/ml | 53 | 83 | +56.6 |

While the present invention has been described and illustrated in conjunction with a number of specific embodiments, those skilled in the art will appreciate that variations and modifications may be made without departing from the principles of the invention as herein illustrated, described and claimed. The invention may be embodied in other specific forms without departing from the spirit or essential characteristics thereof. The present embodiments are to be considered in all respects as illustrative, and not restrictive. The scope of the invention, is therefore, indicated by the appended claims rather than by the foregoing description, and all changes which come within the meaning and range of equivalency of the claims are to be embraced within their scope.

I claim:

1. A composition for promoting anabolic growth in humans and mammals, comprising therapeutically effective amounts of:

(a) at least one androgenic testosterone precursor selected from the group consisting of $\Delta^4$-androstene-3,17-dione, pregnenolone, dehydroepiandrosterone, $\Delta^4$-androstene-3β,17β-diol, $\Delta^5$-androstene-3β,17β-diol, 19-norandrost-4-ene-3,17-dione, 19-norandrost-4-ene-3β,17β-diol, 19-norandrost-5-ene-3β,17β-diol, and pharmaceutically acceptable salts thereof;

(b) at least one natural product having anti-estrogen activity selected from the group consisting of green tea, black tea, catechu, extract thereof and powder thereof;

(c) at least one substance having anti-DHT activity selected from the group consisting of zinc and pharmaceutically acceptable zinc salts; and (d) a pharmaceutically suitable carrier;

wherein said androgenic testosterone precursor promotes anabolic growth while said natural product having anti-estrogen activity reduces estrogen effects associated with the administration of said androgenic testosterone precursor and said substance having anti-DHT activity reduces conversion of said androgenic testosterone precursor to dihydrotestosterone.

2. The composition of claim 1, wherein said androgenic testosterone precursor is selected from the group consisting of $\Delta^4$-androstene-3β,17β-diol and $\Delta^5$-androstene-3β,17β-diol.

3. The composition of claim 1, wherein said composition is in an oral dosage form selected from the group consisting of tablets, capsules, powders, drinks, bars, candies, liquid sprays, gums and liposomal solutions.

4. The composition of claim 1, wherein said pharmaceutically acceptable zinc salt is selected from the group consisting of the acetate, alaninate, alpha-aminobutyrate, arginate, ascorbate, benzoate, butyrate, beta-hydroxybutyrate, n-butyrate, carnosinate, chloride, citrate, formate, glycinate, gluconate, histidinate, iso-leucinate, iso-valinate, leucinate, lysinate, monomethionate, oxide, picolinate, propionate, succinate, sulfate, transferrin, and valinate forms.

5. The composition of claim 1, wherein said substance causes emesis to a mammal taking the composition in excess of a recommended dosage.

6. The composition of claim 1, further comprising copper or a copper salt.

7. A composition for promoting anabolic growth in humans and mammals, comprising therapeutically effective amounts of:
(a) at least one androgenic testosterone precursor selected from the group consisting of $\Delta^4$-androstene-3,17-dione, pregnenolone, dehydroepiandrosterone, $\Delta^4$-androstene-3β, 17β-diol, $\Delta^5$-androstene-3β,17β-diol, 19-norandrost-4-ene-3,17-dione, 19-norandrost-4-ene-3β, 17β-diol, 19-norandrost-5-ene-3β,17β-diol, and pharmaceutically acceptable salts thereof;
(b) at least one natural product having anti-estrogen activity selected from the group consisting of bioflavonoids, catechin polyphenols, glucarates, guaianolides, indoles, isoflavones, phytosterols, resorcyclic acid lactones, saponins, saponin flavones, and tocotrienols; and
(c) at least one substance having anti-DHT activity selected from the group consisting of zinc, pharmaceutically acceptable zinc salts, Saw palmetto berry, *Pygeum africanum*, Green tea, Saw palmetto berry extract, *Pygeum africanum* extract, Green tea extract, *Tribulus terrestris* extract, pumpkin seed oil, pumpkin seed, calcium D-glucarate, and beta-sitosterol;
wherein said androgenic testosterone precursor promotes anabolic growth.

8. The composition of claim 7, wherein said androgenic testosterone precursor is selected from the group consisting of $\Delta^4$-androstene-3,17-dione, dehydroepiandrosterone, $\Delta^4$-androstene-3β,17β-diol, $\Delta^5$-androstene-3β,17β-diol, and pharmaceutically acceptable salts thereof.

9. The composition of claim 7, wherein said substance having anti-DHT activity is a pharmaceutically acceptable zinc salt selected from the group consisting of the acetate, alaninate, alpha-aminobutyrate, arginate, ascorbate, benzoate, butyrate, beta-hydroxybutyrate, n-butyrate, carnosinate, chloride, citrate, formate, glycinate, gluconate, histidinate, iso-leucinate, iso-valinate, leucinate, lysinate, monomethionate, oxide, picolinate, propionate, succinate, sulfate, transferrin, and valinate forms.

10. The composition of claim 7, wherein said natural product having anti-estrogen activity is a catechin polyphenol selected from the group consisting of green tea, black tea, and catechu.

11. The composition of claim 7, wherein said natural product having anti-estrogen activity is a phytosterol selected from the group consisting of alfalfa, soy, soy extract, red clover and red clover extract.

12. The composition of claim 7, wherein said natural product having anti-estrogen activity is selected from the group consisting of citrus fruits, citrus flavonoids, soybeans, pulses, soy germ, bee propolis, alfalfa, clover, 7,8-benzoflavone and Biochanin A.

13. The composition of claim 7, wherein said natural product having anti-estrogen activity is a tocotrienol selected from the group consisting of rice bran, rice bran oil, and palm oil.

14. The composition of claim 7, further comprising a pharmaceutically suitable carrier.

15. The composition of claim 7, wherein said natural product and said substance are different.

16. A composition for promoting anabolic growth in humans, comprising therapeutically effective amounts of:
(a) at least one androgenic testosterone precursor selected from the group consisting of $\Delta^4$-androstene-3,17-dione, pregnenolone, dehydroepiandrosterone, $\Delta^4$-androstene-3β,17β-diol, $\Delta^5$-androstene-3β,17β-diol, 19-norandrost-4-ene-3,17-dione, 19-norandrost-4-ene-3β,17β-diol, 19-norandrost-5-ene-3β,17β-diol, and pharmaceutically acceptable salts thereof;
(b) at least one natural product having anti-estrogen activity in mammals, said natural product reducing estrogen effects associated with the administration of said androgenic testosterone precursor;
(c) at least one substance having anti-DHT activity effective to reduce the production of dihydrotestosterone in prostate tissue; and
(d) a pharmaceutically suitable carrier.

17. A method for promoting anabolic growth in humans, comprising administering to a mammal therapeutically effective amounts of:
(a) at least one androgenic testosterone precursor selected from the group consisting of $\Delta^4$-androstene-3,17-dione, pregnenolone, dehydroepiandrosterone, $\Delta^4$-androstene-3β,17β-diol, $\Delta^5$-androstene-3β,17β-diol, 19-norandrost-4-ene-3,17-dione, 19-norandrost-4-ene-3β,17β-diol, 19-norandrost-5-ene-3β,17β-diol, and pharmaceutically acceptable salts thereof;
(b) at least one natural product having anti-estrogen activity selected from the group consisting of green tea, black tea, catechu, extract thereof and powder thereof;
(c) at least one substance having anti-DHT activity selected from the group consisting of zinc and pharmaceutically acceptable zinc salts; and
(d) a pharmaceutically suitable carrier;
wherein said androgenic testosterone precursor promotes anabolic growth while said natural product having anti-estrogen activity reduces estrogen effects associated with the administration of said androgenic testosterone precursor and said substance having anti-DHT activity reduces conversion of said androgenic testosterone precursor to dihydrotestosterone,
wherein said androgenic testosterone precursor promotes anabolic effects in humans and mammals while said natural product having anti-estrogen activity and said substance having anti-DHT activity inhibit harmful side effects in hormone-responsive tissues.

18. The method of composition of claim 17, wherein said androgenic testosterone precursor is selected from the group consisting of $\Delta^4$-androstene-3β,17β-diol and $\Delta^5$-androstene-3β,17β-diol.

19. The method of claim 17,
wherein said pharmaceutically acceptable zinc salt is selected from the group consisting of the acetate, alaninate, alpha-aminobutyrate, arginate, ascorbate, benzoate, butyrate, beta-hydroxybutyrate, n-butyrate, carnosinate, chloride, citrate, formate, glycinate, gluconate, histidinate, iso-leucinate, iso-valinate, leucinate, lysinate, monomethionate, oxide, picolinate, propionate, succinate, sulfate, transferrin, and valinate forms.

20. The method of claim 17,
further comprising copper or a copper salt.

* * * * *